(12) United States Patent  (10) Patent No.: US 7,162,293 B2
Weiss  (45) Date of Patent: Jan. 9, 2007

(54) MR ARRANGEMENT FOR LOCALIZING A MEDICAL INSTRUMENT

(76) Inventor: Steffen Weiss, Georg-Clasen-Weg 73, D-22415 Hamburg (DE)

( * ) Notice: Subject to any disclaimer, the term of this patent is extended or adjusted under 35 U.S.C. 154(b) by 620 days.

(21) Appl. No.: 10/268,809

(22) Filed: Oct. 10, 2002

(65) Prior Publication Data

US 2003/0073898 A1   Apr. 17, 2003

(30) Foreign Application Priority Data

Oct. 10, 2001  (DE)  ............................ 101 49 955

(51) Int. Cl.
*A61B 5/055*  (2006.01)
(52) U.S. Cl. ...................... 600/411; 600/423; 600/424
(58) Field of Classification Search ................ 600/410, 600/411, 423, 424; 324/307, 309, 318, 322
See application file for complete search history.

(56) References Cited

U.S. PATENT DOCUMENTS 5,353,795 A * 10/1994 Souza et al. ................ 600/423
6,236,205 B1   5/2001 Ludeke
6,397,094 B1 * 5/2002 Ludeke et al. .............. 600/411
6,512,941 B1 * 1/2003 Weiss et al. ................ 600/410

* cited by examiner

*Primary Examiner*—Ruth S. Smith
(74) *Attorney, Agent, or Firm*—Thomas M. Lundin

(57) ABSTRACT

The invention relates to an MR arrangement which includes a medical instrument (3), an RF arrangement (17) which is provided thereon and in which at least one microcoil (1) and a capacitor (2) are connected so as to form a resonant circuit, and also an optical signal lead (4) via which a light signal is applied to the RF arrangement. In order to achieve simple and fast determination of the position of the medical instrument (3) within the examination zone of an MR apparatus, the invention proposes to provide a modulator (20) for modulating the light signal applied to the RF arrangement and also an optoelectrical converter (5) which converts the modulated light signal into an electrical signal and is coupled to the resonant circuit in such a manner that the resonant circuit is triggered by the electrical signal from the optoelectrical converter (5) so as to emit an RF field.

17 Claims, 2 Drawing Sheets

MR ARRANGEMENT FOR LOCALIZING A MEDICAL INSTRUMENT

BACKGROUND

The invention relates to an MR arrangement which includes a medical instrument, an RF arrangement which is provided thereon and in which at least one microcoil and a capacitor are connected so as to form a resonant circuit, and also includes an optical signal lead via which a light signal is applied to the RF arrangement.

The invention also relates to a method of localizing a medical instrument in the examination volume of an MR apparatus, which medical instrument includes an RF arrangement in which at least one microcoil and a capacitor are connected so as to form a resonant circuit, and also an optical signal lead via which a light signal is applied to the RF arrangement, the position of the medical instrument being determined from the MR signal generated by the microcoil in the vicinity thereof.

The invention also relates to a medical instrument, notably an intravascular catheter, a guide wire or a biopsy needle, which includes an RF arrangement which is provided at the distal end and in which at least one microcoil and a capacitor are connected so as to form a resonant circuit, and also an optical signal lead via which a modulated light signal is applied to the RF arrangement, and also relates to an MR apparatus provided with such a medical instrument.

The localization of interventional instruments is important in medicine, that is, both in diagnostic and in therapeutic methods. Such instruments may be, for example, intravascular catheters, biopsy needles, minimal-invasive surgical instruments or the like. An important application of interventional radiology is formed by angiography which is intended to uncover the anatomical details of the vascular system of a patient.

Angiography methods based on magnetic resonance tomography (MR) are becoming increasingly more important nowadays. In comparison with X-ray diagnostics as customarily practiced thus far, magnetic resonance offers the major advantage of significantly enhanced tissue selectivity. MR techniques are known in which a microcoil for the detection of magnetic resonance signals is provided on an interventional instrument. Of particular interest in this respect are MR methods for the examination of blood vessels by means of intravascular catheters whose tip is provided with such a microcoil.

An elementary problem encountered in such MR-assisted angiography methods is that long electrical connection leads which extend along the entire length of the intervascular catheter are required so as to transfer the RF MR signal from the microcoil mounted at the tip of the catheter to the electronic receiving circuit of the MR system used. The strong RF radiation in the examination zone may give rise to undesirable and hazardous heating phenomena in such connection wires. The RF fields within the examination zone are capable of generating standing waves in the cables extending within the catheter, thus giving rise to resonant RF heating of the cable. The use of intravascular catheters with long cables extending therein is hampered by second thoughts concerning the safety of such arrangements. The described phenomena can be calculated only with difficulty, because the resonant RF heating is dependent on the field distributions of the RF fields as well as on the geometrical and electrical properties of the electrical leads and their dielectric environment. During experiments sudden intense heating has occurred which could give rise to life-threatening injuries of a patient to be examined.

The risk of resonant RF heating is completely avoided when an optical transmission technique is used for the transmission of the MR signals.

U.S. Pat. No. 6,236,205 B1 discloses an MR device with a medical instrument and a method for localizing the medical instrument in which a resonant circuit which is mounted on the medical instrument is influenced by way of an optical control signal which is applied to the resonant circuit via an optical fiber. At least one microcoil forms part of said resonant circuit. In conformity with the known method first an RF excitation is carried out in a customary manner in the entire examination volume of interest. The nuclear magnetization thus produced in the vicinity of the medical instrument induces a voltage in the microcoil. The resonant circuit thus triggered subsequently emits an RF signal whereby the MR signal in the vicinity of the microcoil is intensified and modified. According to the known method the resonant circuit is alternately switched on and off by way of an optically controllable impedance by variation in time of the optical control signal. As a result, the RF signal emitted by the microcoil also varies in time in conformity with the control signal so that it can be distinguished from the background signal. This feature of distinction is used for determining the position of the medical instrument.

The major drawback of the known method resides in the fact that the magnetization excitation must be excited in the entire examination volume. In order to determine the position, use is made of a difference signal which represents the difference between the MR signals detected while the resonant circuit is switched on and off. In this difference signal the weak local signal of the resonant circuit has to compete with the strong background signal of the entire examination volume. Therefore, the signal-to-noise ratio of the measuring signal available for determining the position is comparatively poor.

It is a further drawback that the known method requires a significant amount of additional measuring time. It is first necessary either to generate complete images or to make repeatedly projections in each of the three spatial directions in order to enable the position of the medical instrument to be found by differentiation. The repetition in the case of the projections is necessary to increase the signal-to-noise ratio of the measuring signal by averaging.

Moreover, it is a drawback that the known method is very susceptible to motional artefacts. When the position of the medical instrument is changed in the course of the measurement, errors are introduced in the image data and reliable localization is strongly impeded.

SUMMARY

It is an object of the present invention to provide an improved MR arrangement in which notably the described drawbacks are avoided.

On the basis of an MR arrangement of the kind set forth, this object is achieved by means of a modulator for modulating the light signal applied to the RF arrangement, and by means of an optoelectrical converter which converts the modulated light signal into an electrical signal and is coupled to the resonant circuit in such a manner that the resonant circuit is triggered by the electrical signal from the optoelectrical converter so as to emit an RF field.

In the arrangement in accordance with the present invention the modulated light signal is converted into an electrical signal by means of the optoelectrical converter, so that the resonant circuit is triggered so as to emit an RF signal. Under the influence of the emitted RF signal, nuclear magnetization is generated in the immediate physical vicinity of the microcoil. This local nuclear magnetization can be readily detected as an MR signal by means of the external receiving coils of the MR apparatus so as to be used for localization without intricate processing, that is, merely by frequency analysis in the simplest case.

As opposed to the known arrangement, the arrangement in accordance with the invention utilizes the optoelectrical converter instead of the optically controlled impedance; this converter serves to some extent as a current source for the resonant circuit, thus enabling the active generation of local nuclear magnetization. To this end, the light signal is modulated with the resonance frequency of the MR apparatus used.

In comparison with the known method, the localization by means of the arrangement in accordance with the invention is performed by a local RF excitation and not by an overall RF excitation. This offers the advantage that the described intricate and error prone differentiating method is completely abandoned for the localization. The localization by means of the arrangement in accordance with the invention advantageously requires only a minimum measuring time. Consequently, motional artefacts do not form a problem.

In accordance with one aspect of the present invention, the optoelectrical converter of the arrangement in accordance with the invention may advantageously be a simple photodiode. The excitation of the resonant circuit is then realized by the photocurrent generated in the photodiode by the modulated light signal. Suitable photodiodes are advantageously commercially available as inexpensive compact components.

In accordance with another aspect of the present invention, the microcoil, the capacitor and the photodiode in the resonant circuit are connected in parallel. This results in a parallel resonant circuit which consists of the microcoil and the capacitor and in which the photocurrent of the equally parallel connected photodiode is fed directly into the parallel resonant circuit.

The arrangement in accordance with the invention can be used for a method for localizing a medical instrument, wherein the medical instrument includes an RF arrangement in which at least one microcoil and a capacitor are connected so as to form a resonant circuit, and also includes an optical signal lead via which a light signal is applied to the RF arrangement, and the position of the medical instrument is determined from the MR signal generated by the microcoil in the vicinity thereof, and the MR signal is generated by coupling a light signal which is modulated with the resonance frequency of the MR apparatus into the optical signal lead, which light signal is converted, by means of an optoelectrical converter which is coupled to the resonant circuit, into an electrical signal whereby the resonant circuit is triggered so as to emit an RF field at the resonance frequency of the MR apparatus.

In order to generate the local nuclear magnetization, or the detectable MR signal, it is advantageous to couple in the modulated light signal in a pulsed fashion. The light signal is coupled in as a light pulse, the light signal at the same time being modulated with the resonance frequency of the MR apparatus. The optoelectrical converter generates an RF pulse from said light pulse, which RF pulse corresponds to the customary RF pulses used to generate nuclear magnetization. The duration and shape of the pulse can be adapted in such a manner that optimum excitation is achieved. The choice of the relevant parameters is dependent on the desired spatial resolution during the localization as well as on the amplitude of the MR signals required for the detection.

Alternatively, the light is continuously coupled in, in which case merely the modulation with the resonance frequency of the MR apparatus takes place in a pulsed fashion. This may be advantageous when, for example, a photodiode whose impedance is dependent on the light coupled in is used as the optoelectrical converter. The impedance of the photodiode directly influences the resonance properties of the resonant circuit. The resonant circuit can be simply tuned in such a manner that the resonance condition is satisfied when the photodiode is exposed, that is, when a photocurrent flows. This also offers the advantage that the resonant circuit is in resonance also during the detection phase, so that the MR signal from the vicinity of the medical instrument is additionally intensified.

In accordance with another aspect of the present invention, a medical instrument, notably an intravascular catheter, guide wire or biopsy needle, is provided which includes an RF arrangement which is provided at the distal end and in which at least one microcoil and a capacitor are connected so as to form a resonant circuit, and also an optical signal lead via which a modulated light signal is applied to the RF arrangement, the resonant circuit is coupled to a photodiode, in which the modulated light signal generates a photocurrent, in such a manner that the resonant circuit is triggered by the photocurrent so as to emit an RF field.

In accordance with another aspect of the invention, the microcoil, the capacitor and the photodiode are connected in parallel in the resonant circuit.

In accordance with another aspect of the invention, there is provided an additional blocking capacitor which is connected in series with the photodiode.

It is advantageous to include an additional blocking capacitor in the parallel connection consisting of the microcoil, the capacitor and the photodiode. The blocking capacitor blocks the DC component of the photodiode and keeps it away from the resonant circuit. In the absence of the blocking capacitor there is a risk of heating of the microcoil. The blocking capacitor also offers the advantage that the operating point of the photodiode, and hence also its impedance, can be changed by varying the DC component in the light signal. This aspect can be used for the fine tuning of the resonant circuit which may be necessary due to changes of the resonance frequency of the resonant circuit as caused by changes of the dielectric environment, temperature drift or geometrical deformation of the microcoil.

In accordance with another aspect of the present invention an MR apparatus is provided which includes at least one main field coil, a number of gradient coils, at least one control unit, at least one receiving coil which is connected to a receiving unit, a data processing unit and a medical instrument which includes an RF arrangement in which at least one microcoil and a capacitor are connected so as to form a resonant circuit, the RF arrangement being supplied with a light signal via an optical signal lead, the light of a light source is modulated by means of a modulator prior to being coupled into the optical signal lead, and the modulated light signal is converted into an electrical signal by means of an optoelectrical converter which is coupled to the resonant circuit in such a manner that the resonant circuit is triggered by the electrical signal from the optoelectrical converter so as to emit an RF field.

DRAWINGS

Embodiments of the invention will be described in detail hereinafter, by way of example, with reference to the drawings. Therein:

DESCRIPTION

Figure 1:
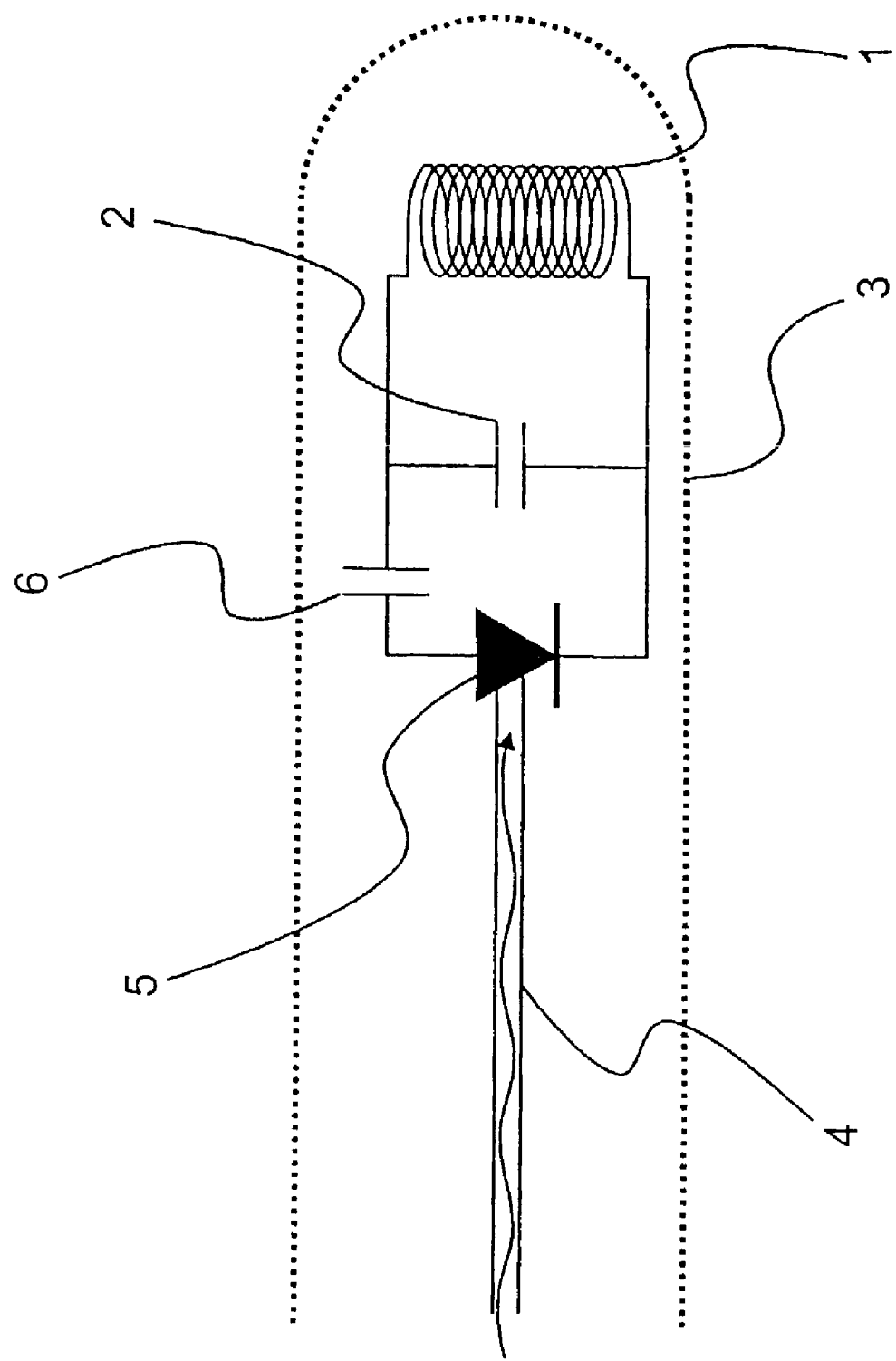
FIG. 1 shows an intravascular catheter in accordance with the invention.

FIG. 1 shows that in accordance with the invention it is possible to integrate an RF arrangement, in which a microcoil 1 and a capacitor 2 are connected so as to form a resonant circuit, in the tip of an intervascular catheter 3. The RF arrangement receives a light signal via a signal lead 4. The signal lead 4 may be, for example, a conventional glass fiber. In the embodiment shown in FIG. 1 a photodiode 5 is used as the optoelectrical converter. The modulated light signal, applied to the photodiode 5 via the optical fiber 4, generates a photocurrent in the photodiode 5. The light signal is modulated with the frequency of the resonant circuit, so that the latter is triggered to resonance by the resultant RF photocurrent. Because of the AC current then flowing in the resonant circuit, the microcoil 1 emits an RF field in the vicinity of the tip of the catheter 3. The arrangement shown in FIG. 1 also includes a blocking capacitor 6 which keeps the DC component of the photocurrent generated in the photodiode 5 away from the resonant circuit. The impedances of the photodiode 5 and the blocking capacitor 6 influence the resonance behavior of the RF arrangement. It is advantageous to tune the resonant circuit in such a manner that the resonance frequency has the desired value when the photodiode is in the active state, that is, the illuminated state. Varying the intensity of the light signal coupled in then advantageously enables fine tuning of the resonant circuit within given limits, for example, so as to compensate changes in the dielectric vicinity of the circuit, drift due to temperature effects or geometrical deformations of the microcoil.

Figure 2:
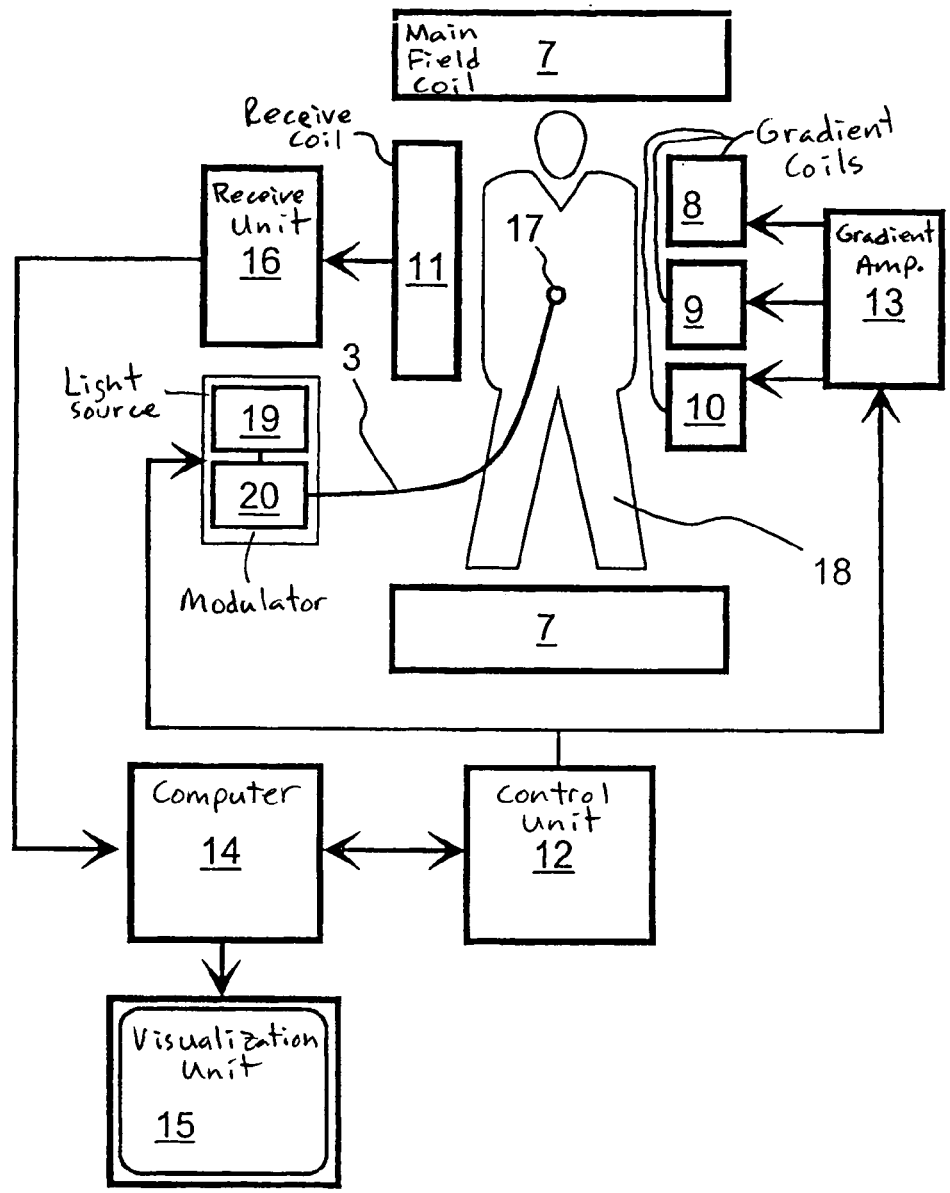
FIG. 2 shows an MR apparatus in accordance with the invention.

FIG. 2 shows a block diagram of an MR apparatus provided with an arrangement in accordance with the invention. The system consists of a main field coil 7 for generating a steady, uniform magnetic field, gradient coils 8, 9 and 10 for generating magnetic field gradients in the X, the Y and the Z direction, and a receiving coil 11 for the detection of MR signals in the examination volume of the MR apparatus. The variation in time of the magnetic field gradient is controlled by means of a control unit 12 which is connected to the gradient coils 8, 9 and 10 via a gradient amplifier 13. The system also includes a reconstruction unit in the form of a microcomputer 14 as well as a visualization unit 15, for example, in the form of a graphic monitor. The receiving coil 11 is connected, via a receiving unit 16, to the reconstruction unit 14 which processes the detected MR signals so as to reproduce these signals in a suitable manner by way of the visualization unit 15. The receiving unit 16 operates in a conventional manner and demodulates the MR signal so as to convert it with an as narrow band as possible into a low-noise RF measuring signal.

The RF arrangement of the catheter 3 is denoted in its entirety by the reference numeral 17 in FIG. 2. The catheter 3 is introduced into a patient 18. The RF arrangement 17 is connected, via the optical fiber 4 which extends in the catheter 3, to a light source 19 and a modulator 20 for modulating the light of the light source 19. The light source 19 and the modulator 20 are controlled by the control unit 12 which controls the variation in time of the light signal coupled in. The modulator 20 may be, for example, a Pockels cell in which a crystal of an electro-optical material is arranged between two crossed polarizers. The light intensity coupled into the optical signal lead 4 of the catheter 3 is then proportional to an RF AC voltage which is applied to the modulator 20 and whose variation in time is imposed by the control unit 12.

During the examination the catheter 3 is situated in a blood vessel within the patient 18. The RF field emitted by the microcoil locally generates nuclear magnetization in the tissue which directly surrounds the tip of the catheter, which nuclear magnetization can be detected as an MR signal by the external receiving coil 11 of the MR apparatus. When magnetic field gradients are suitably imposed on the magnetic field generated by the main field coil 7, the desired position information is encoded in the frequency of the MR signal originating from the vicinity of the tip of the catheter. The position of the tip of the catheter 3 within the patient is then derived simply by determining the frequency of the detected MR signal. The frequency analysis of the MR signal is performed by means of the reconstruction unit 14 which then displays the position of the tip of the catheter on the monitor 15.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An MR apparatus comprising:
    a medical instrument;
    an RF arrangement disposed on the medical instrument, the RF arrangement comprising:
        at least one microcoil; and
        a capacitor connected to the microcoil so as to form a resonant circuit;
    an optical signal lead via which a light signal is applied to the RF arrangement;
    a modulator for modulating the light signal applied to the RF arrangement; and
    an optoelectrical converter for converting the modulated light signal into an electrical signal, the optoelectrical converter being coupled to the resonant circuit in such a manner that the resonant circuit is triggered by the electrical signal from the optoelectrical converter so as to emit an RF field.

2. An MR arrangement as claimed in claim 1, wherein the optoelectrical converter is a photodiode.

3. An MR arrangement as claimed in claim 2, wherein the microcoil, the capacitor and the photodiode are connected in parallel in the resonant circuit.

4. A method of localizing a medical instrument in an examination volume of an MR apparatus having an RF frequency, the method comprising:
    generating a light signal;
    coupling the light signal along an optical signal lead to a optoclectrical converter;
    converting the light signal to a photocurrent using the optoelectrical converter; and
    emitting an RF field in the vicinity of the medical instrument in response to the photocurrent using a resonant circuit disposed on the medical instrument wherein the light signal is modulated with the resonance frequency of the MR apparatus into the optical signal lead.

5. The method according to claim 4 wherein the resonant circuit comprises at least one coil and at least one capacitor.

6. The method according to claim 4 wherein the RF field in the vicinity of the medical instrument is at the resonance frequency of the MR apparatus.

7. A method as claimed in claim 4 wherein the modulated light signal is coupled into the optical signal lead in a pulsed fashion, the MR signal generated in the vicinity of the microcoil being detected each time subsequent to a light pulse in order to be evaluated for the determination of the position.

8. A method as claimed in claim 4 wherein the light signal coupled into the optical signal lead is modulated with the resonance frequency of the MR apparatus in a pulsed fashion, the MR signal generated in the vicinity of the microcoil being detected each time in the time intervals in which the light signal is not modulated.

9. A medical instrument comprising:
   an RF arrangement disposed at the distal end of the medical instrument, the RF arrangement comprising at least one microcoil and a capacitor connected so as to form a resonant circuit; and
   an optical signal lead via which a modulated light signal is applied to the RF arrangement;
   wherein the resonant circuit is coupled to a photodiode, in which the modulated light signal generates a photocurrent, in such a manner that the resonant circuit is triggered by the photocurrent so as to emit an RF field.

10. A medical instrument as claimed in claim 9, wherein the microcoil, the capacitor and the photodiode are connected in parallel in the resonant circuit.

11. A medical instrument as claimed in claim 10, wherein there is provided an additional blocking capacitor which is connected in series with the photodiode.

12. An MR apparatus which includes at least one main field coil, a plurality of gradient coils, at least one control unit, at least one receiving coil connected to a receiving unit, a data processing unit and a medical instrument which includes an RF arrangement in which at least one microcoil and a capacitor are connected so as to form a resonant circuit, the RF arrangement being supplied with a light signal via an optical signal lead, wherein the light of a light source is modulated by means of a modulator prior to being coupled into the optical signal lead, and that the modulated light signal is converted into an electrical signal by means of an optoelectrical converter which is coupled to the resonant circuit in such a manner that the resonant circuit is triggered by the electrical signal from the optoelectrical converter so as to emit an RF field.

13. A medical instrument having a length and a distal end, the medical instrument for use in a magnetic resonance system and comprising:
   a coil disposed at the distal end of the medical instrument;
   a capacitor in electrical connection with the coil, the coil and capacitor forming a resonant circuit; and
   an optoelectrical converter in electrical connection with the resonant circuit, the optoelectrical converter for receiving a light signal from a signal lead, the signal lead disposed along the length of the medical instrument and for converting the light signal to a photocurrent which triggers resonance in the resonance circuit.

14. A medical instrument as set forth in claim 13 wherein the optoelectrical converter comprises a photodiode.

15. A medical instrument as set forth in claim 13 further comprising:
   a blocking capacitor in electrical connection with the resonant circuit, the blocking capacitor for keeping a DC component of the photocurrent away from the resonant circuit.

16. A medical instrument as set forth in claim 13, the coil for emitting an RF field in the vicinity of the distal end of the medical instrument in response to an AC component of the photocurrent.

17. A magnetic resonance apparatus comprising:
   a main field coil for generating a generally steady, uniform magnetic field in an examination region;
   a plurality of gradient coils for generating magnetic field gradients in the examination region;
   a radio frequency receive coil for receiving magnetic resonance signals from a subject disposed in the examination region and from a medical instrument disposed within the examination region, the medical instrument comprising:
   a coil disposed at the distal end of the medical instrument;
   a capacitor in electrical connection with the coil, the coil and capacitor forming a resonant circuit; and
   an optoelectrical converter in electrical connection with the resonant circuit, the optoelectrical converter for receiving a light signal from a signal lead, the signal lead disposed along the length of the medical instrument and for converting the light signal to a photocurrent which triggers resonance in the resonance circuit.

* * * * *